United States Patent
Dasbach et al.

(10) Patent No.: US 9,302,057 B2
(45) Date of Patent: Apr. 5, 2016

(54) NEEDLE ASSEMBLY REUSE PREVENTION MECHANISM

(75) Inventors: Uwe Dasbach, Frankfurt am Main (DE); Verena Hofmann, Frankfurt am Main (DE); Peter Nober, Rommersheim (DE); Leo Zeimetz, Büttelborn (DE); Thorsten Mutter, Dorsheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 50 days.

(21) Appl. No.: 14/114,316

(22) PCT Filed: Apr. 27, 2012

(86) PCT No.: PCT/EP2012/057794
§ 371 (c)(1),
(2), (4) Date: Oct. 28, 2013

(87) PCT Pub. No.: WO2012/146728
PCT Pub. Date: Nov. 1, 2012

(65) Prior Publication Data
US 2014/0046256 A1    Feb. 13, 2014

(30) Foreign Application Priority Data

Apr. 29, 2011  (EP) .................................. 11164286

(51) Int. Cl.
*A61M 5/50*  (2006.01)
*A61M 5/32*  (2006.01)
*A61B 19/02*  (2006.01)
*A61M 5/00*  (2006.01)

(52) U.S. Cl.
CPC ................. *A61M 5/50* (2013.01); *A61M 5/002* (2013.01); *A61M 5/3205* (2013.01); *A61B 19/0262* (2013.01); *A61M 5/321* (2013.01); *A61M 5/3271* (2013.01); *A61M 2005/004* (2013.01); *A61M 2005/005* (2013.01); *A61M 2205/584* (2013.01)

(58) Field of Classification Search
CPC ............ A61M 5/3257; A61M 5/3271; A61M 5/3219; A61M 5/3243; A61M 5/321; A61M 5/3205; A61M 5/002; A61M 2005/004; A61M 2005/005; A61M 5/1626; A61B 19/02662; A61B 19/0262
See application file for complete search history.

(56) References Cited

U.S. PATENT DOCUMENTS

| | | | |
|---|---|---|---|
| 5,591,138 A * | 1/1997 | Vaillancourt | 604/263 |
| 5,873,462 A | 2/1999 | Nguyen et al. | |
| 6,302,868 B1 * | 10/2001 | Mohammad | 604/192 |
| 6,613,022 B1 * | 9/2003 | Doyle | 604/192 |
| 2003/0014018 A1 * | 1/2003 | Giambattista et al. | 604/198 |
| 2008/0058732 A1 | 3/2008 | Harris | |
| 2011/0066114 A1 * | 3/2011 | McDown et al. | 604/192 |

FOREIGN PATENT DOCUMENTS

| | | |
|---|---|---|
| EP | 2223714 A1 | 9/2010 |
| GB | 2459772 A | 11/2009 |
| WO | 0210465 A1 | 2/2002 |

* cited by examiner

*Primary Examiner* — Bhisma Mehta
*Assistant Examiner* — Nilay Shah
(74) *Attorney, Agent, or Firm* — Fish & Richardson P.C.

(57) ABSTRACT

Described is a needle assembly reuse prevention mechanism comprising a barrier movable between a retracted position and an extended position, a spring coupled to the barrier, a pin formed on the barrier, and a slot receiving the pin. When in the extended position, the barrier substantially covers an opening of a needle assembly storage compartment. The spring forces the barrier in a first direction. The slot has at least one abutment face for abutting the pin and preventing movement of the barrier in the first direction.

19 Claims, 2 Drawing Sheets

NEEDLE ASSEMBLY REUSE PREVENTION MECHANISM

CROSS REFERENCE TO RELATED APPLICATIONS

The present application is a U.S. National Phase Application pursuant to 35 U.S.C. §371 of International Application No. PCT/EP2012/057794 filed Apr. 27, 2012, which claims priority to European Patent Application No. 11164286.4 filed Apr. 29, 2011. The entire disclosure contents of these applications are herewith incorporated by reference into the present application.

FIELD OF INVENTION

The invention relates a needle assembly reuse prevention mechanism for a needle assembly storage device.

BACKGROUND

Patients suffering from diseases like diabetes have to frequently self-administer injections. Injection devices like auto-injectors or pen injectors have been developed to facilitate self-administering injections. Typically, such injection devices are re-usable and refitted with sterile, single-use injection needle assemblies to minimize the risk of infections.

Needle assembly storage devices, like needle assembly magazines or needle assembly dispensers, contain a plurality of such sterile injection needle assemblies that are adapted to be mounted to the injection devices and facilitate storage and transport of the needle assemblies. Additionally, the needle assembly storage device may be used as a disposal container for used injection needles to reduce the risk of accidental needle stick injuries caused by contaminated injection needles. However, there exists a need to prevent reuse of a used needle assembly, e.g., for preventing infection or other injury.

SUMMARY

It is an object of the present invention to provide a needle assembly reuse prevention mechanism for a needle assembly storage device.

In an exemplary embodiment, a needle assembly reuse prevention mechanism comprises a barrier movable between a retracted position and an extended position, a spring coupled to the barrier, a pin formed on the barrier, and a slot receiving the pin. When in the extended position, the barrier substantially covers an opening of a needle assembly storage compartment. The spring forces the barrier in a first direction. The slot has at least one abutment face for abutting the pin and preventing movement of the barrier in the first direction.

In an exemplary embodiment, the barrier comprises a stem and an arm. The arm may have a first portion connected to the stem and a second portion connected to the first portion. The pin may be disposed on a first lateral surface of the second portion. The barrier may also include a ledge formed on a second lateral surface of the second portion. The ledge at least partially covers the opening of the needle assembly storage compartment. The barrier may also include a resetting member for engaging the needle assembly storage compartment. Movement of the needle assembly storage compartment moves the barrier in a second direction, opposite the first direction.

In an exemplary embodiment, the at least one abutment face comprises a first abutment face, a second abutment face and a third abutment face. When the pin abuts the first abutment face, the barrier is in the retracted position. When the pin abuts the second abutment face, the barrier is in an intermediate position. When the pin abuts the third abutment face, the barrier is in the extended position.

In an exemplary embodiment, the pin disengages the first abutment face and the spring forces the barrier in the first direction into the intermediate position when a force is applied to the ledge in a direction substantially perpendicular to the first direction. The pin disengages the second abutment face and the spring forces the barrier in the first direction into the extended position when the force is applied to the ledge in the direction substantially perpendicular to the first direction. The barrier can only move in the second direction when the pin abuts the third abutment face.

In an exemplary embodiment, the barrier includes a visual indicator that can be viewed when the barrier is in the extended position.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
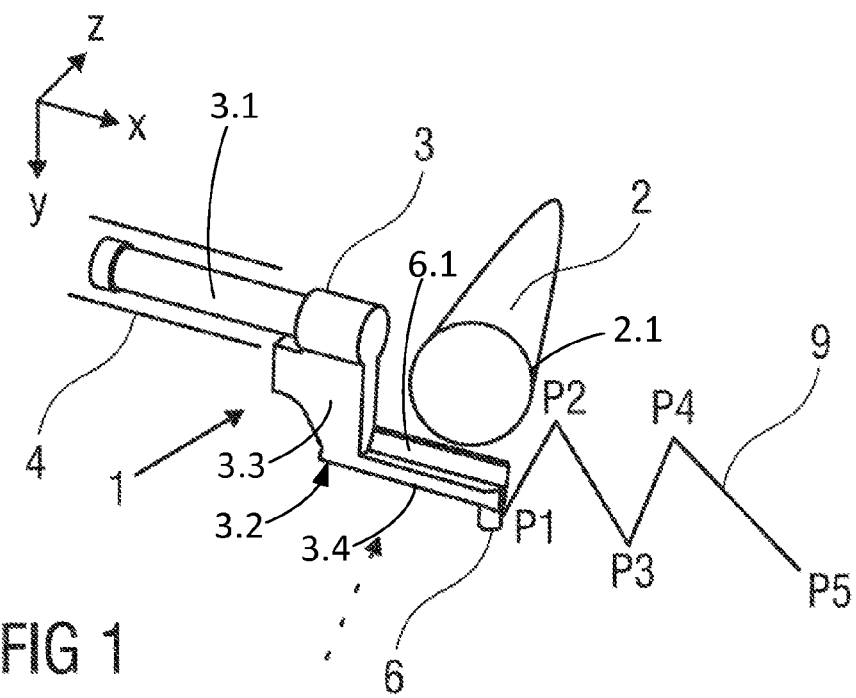
FIG. 1 shows schematically a perspective view of a reuse prevention mechanism and a needle assembly storage compartment according to an exemplary embodiment of the present invention.

FIG. 1 shows schematically a perspective view of an exemplary embodiment of a needle assembly reuse prevention mechanism 1 and a needle assembly storage compartment 2. The needle assembly reuse prevention mechanism 1 may be formed integrally with or coupled to a needle assembly storage device 13, such as a needle magazine, and the needle assembly storage compartment 2 may be one of a plurality of interconnected storage compartments forming an array (e.g., a ring-shaped array of needle assembly storage compartments). The array may be movably disposed within the needle assembly storage device 13 such that unused needle assemblies can be stored and transported by the user and used needle assemblies can be returned to the needle assembly storage compartments after use (for disposal). A needle assembly, such as that used with an injection device (e.g., pen injector and/or autoinjector), may be housed within the needle assembly storage compartment 2.

Figure 3:
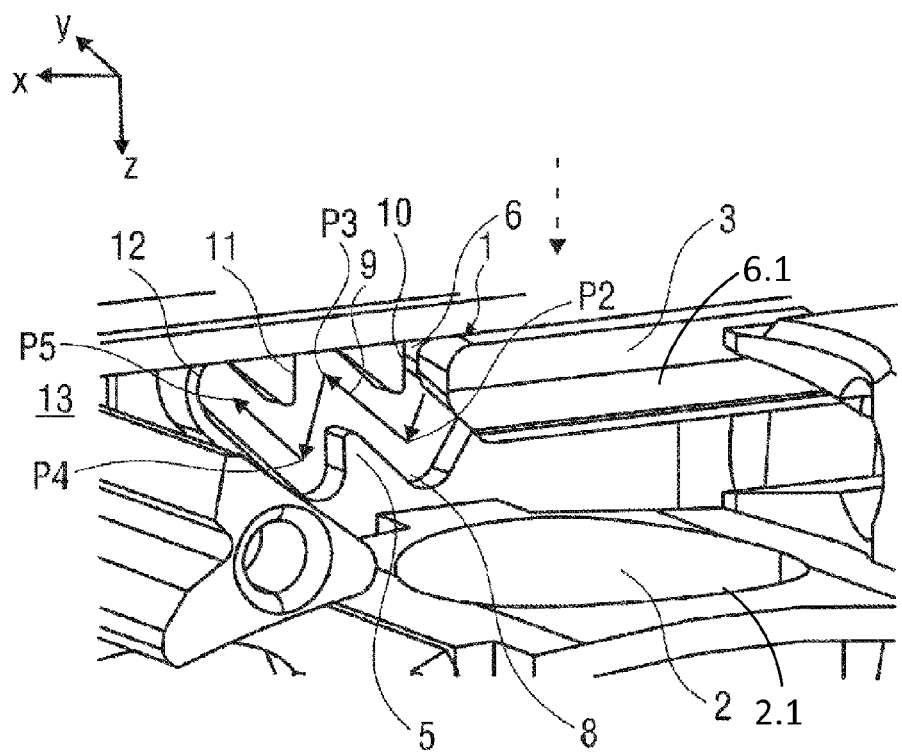
FIG. 3 shows a cut-out of a first perspective view of a needle assembly storage device having a reuse prevention mechanism according to an exemplary embodiment of the present invention.

In an exemplary embodiment, the reuse prevention mechanism 1 comprises a movable barrier 3 which engages a guide device 5 (see FIG. 3) to selectively cover (in an extended position) and uncover (in a retracted position) an opening 2.1 of the needle assembly storage compartment 2. The barrier 3 includes a stem 3.1 which resides in a linear bearing 4 and is moveable in two dimensions (e.g., in the x- and z-directions as shown in FIG. 3). The stem 3.1 may include a spring for urging the barrier 3 in a first direction. In another exemplary embodiment, the stem 3.1 may be rotatable within the linear bearing 4 and axially moveable in one dimension (e.g., in the x-direction as shown in FIG. 3).

An arm 3.2 may be coupled to an end of the stem 3.1. In an exemplary embodiment, the arm 3.2 may comprise a first portion 3.3 connected to the end of the stem 3.1 and a second portion 3.4 connected to an end of the first portion 3.3 such that the first and second portions 3.3, 3.4 form a right angle. In an exemplary embodiment, the first and second portions 3.3, 3.4 are configured so that they do not obstruct the opening 2.1 of the needle assembly storage compartment 2, thereby allowing an injection device to access the needle assembly therein.

The second portion 3.4 of the arm 3.2 includes a pin 6 for mating with a guideway 8 formed in the needle assembly storage device. The pin 6 may be formed on a first lateral surface of the second portion 3.4 and a ledge 6.1 may be formed on a second lateral surface of the second portion 3.4, opposite the first lateral surface. The ledge 6.1 may be a projection which extends at least partially over the opening 2.1 of the needle assembly storage compartment 2. A resetting member 7 (shown in FIG. 4) may be formed on an inferior surface of the second portion 3.4. The resetting member 7 may selectively engage a border of the needle assembly storage compartment 2 to move the barrier 3 from its extended position to its refracted position, as described further below.

Figure 2:
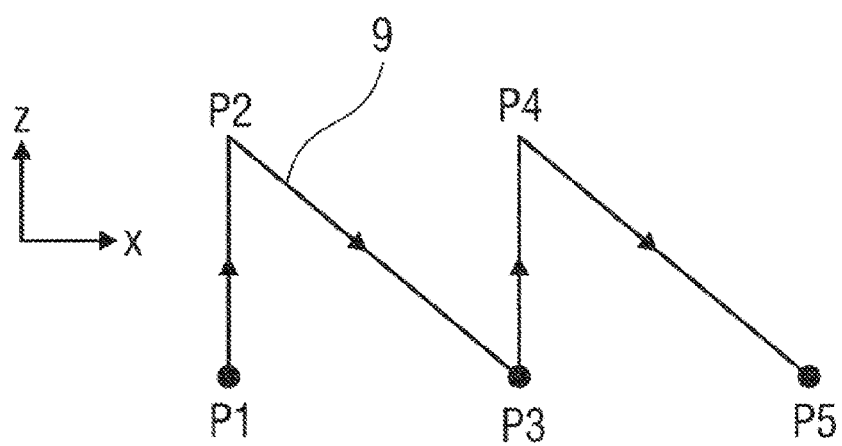
FIG. 2 shows schematically a guideway of a reuse prevention mechanism according to an exemplary embodiment of the present invention.

As shown in the exemplary embodiment of FIG. 3, the barrier 3 is in the retracted position, and there is an unused needle assembly in the needle assembly storage compartment 2. In the retracted position, the pin 6 of the barrier 3 is in a first position P1 of a slot 9. In an exemplary embodiment, the slot 9 is formed in the needle storage device 13 and the slot 9 is shaped like the letter W (shown inverted in FIG. 2). In the first position P1, the spring force urges the barrier 3 in a first horizontal direction (x-direction as shown in FIG. 3), but movement in the first direction is prevented because the pin 6 abuts a first abutment face 10 of the slot 9.

As the injection device is inserted into the needle assembly storage compartment 2 to engage a needle assembly therein (dashed arrow shown in FIG. 3), the injection device applies force in a first vertical direction (z-direction substantially perpendicular to the first horizontal direction) to the ledge 6.1, the barrier 3 (and the pin 6) to be deflected in the first vertical direction which results in the pin 6 moving to a second position P2 within the slot 9. In an exemplary embodiment, a distal end of the injection device applies a force on the ledge 6.1, displacing the barrier 3 in the first vertical direction. While the injection device is being coupled to the needle assembly in the needle assembly storage compartment 2, the barrier 3 is maintained in a position (and the pin 6 is maintained in the second position P2), because the ledge 6.1 abuts the injection device.

After the needle assembly has been coupled to the injection device and as the injection device is being withdrawn from the needle assembly storage device 13, the spring force causes the barrier 3 to move in the first direction, and a first angled surface of the slot 9 guides the pin 6 into a third position P3. A second abutment face 11 on the slot 9 abuts the pin 6 and prevents the barrier 3 from moving in the first direction, maintaining the barrier 3 in an intermediate position.

In an exemplary embodiment, the same movements of the barrier 3 are repeated when the injection device is re-inserted into the needle assembly storage device to deposit a used needle assembly in the needle assembly storage compartment 2. As the injection device is inserted into the needle assembly storage compartment 2 to deposit the used needle assembly therein, the injection device applies force in the first vertical direction (z-direction substantially perpendicular to the first horizontal direction), causing the barrier 3 (and the pin 6) to be deflected in the first vertical direction which results in the pin 6 moving to a fourth position P4 within the slot 9. In an exemplary embodiment, a distal end of the injection device applies a force on the ledge 6.1, displacing the barrier 3 in the first vertical direction. While the injection device depositing the needle assembly in the needle assembly storage compartment 2, the barrier 3 is maintained in a position (and the pin 6 is maintained in the fourth position P2), because the ledge 6.1 abuts the injection device.

After the used needle assembly has been deposited in the needle assembly storage compartment 2 and as the injection device is being withdrawn from the needle assembly storage device, the spring force causes the barrier 3 to move in the first horizontal direction, and a second angled surface of the slot 9 guides the pin 6 into a fifth position P5. A third abutment face 12 on the slot 9 abuts the pin 6 and prevents the barrier 3 from moving in the first horizontal direction.

When the pin 6 is in the fifth position P5, the barrier 3 is in the extended position. Because the pin 6 cannot move to a position in the first horizontal or vertical directions when it is in the fifth position P5, an attempt to insert the injection device into the needle assembly storage compartment 2 with a used needle assembly will be blocked by the barrier 3. For example, the force of the injection device in the first vertical direction will not displace the barrier 3, and the injection device will abut the barrier 3 (and/or the ledge 6.1).

When the pin 6 is in the fifth position P5, a color and/or label may be printed on a visual surface of the barrier 3 to provide a visual indicator to the user that the needle assembly storage compartment 2 contains a used needle assembly.

Figure 4:
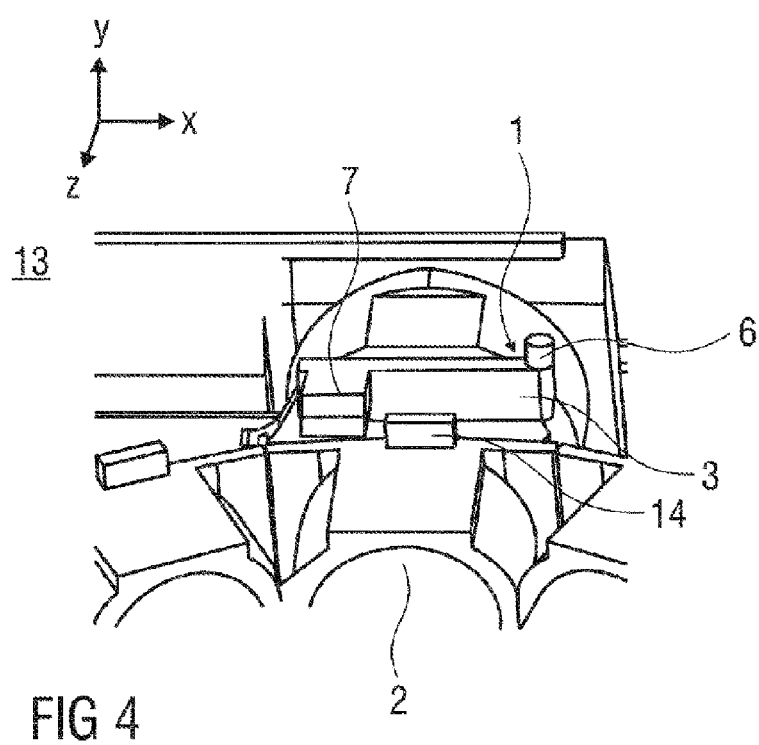
FIG. 4 shows a cut-out of a second perspective view of a needle assembly storage device having a reuse prevention mechanism according to an exemplary embodiment of the present invention.

As shown in the exemplary embodiment of FIG. 4, the barrier 3 can be returned to the retracted position when the array is advanced to a next needle assembly storage compartment with an unused needle assembly. When the array is advanced, a projection 14 formed on the needle assembly storage compartment 2 (or the next needle assembly storage compartment) abuts the resetting member 7 on the barrier 3 and pushes the barrier 3 in a second horizontal direction to the retracted position. As the barrier 3 is pushed in the second horizontal direction, the pin 6 is moved (against the spring force) through each of the positions P5, P4, P3, P2 and finally P1, where the first abutment face 10 prevents movement of the barrier 3 in the first horizontal direction.

Those of skill in the art will understand that the slot 9 may have three positions if a used needle assembly is not to be deposited in the needle assembly storage compartment 2.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle assembly reuse prevention mechanism comprising:
   a barrier movable between a retracted position and an extended position, the barrier comprising a stem and an arm, the arm having a first portion connected to the stem and a second portion connected to the first portion at a right angle, the stem comprising a spring coupled to the barrier, and the spring biasing the barrier in a first direction, wherein when in the extended position, the barrier substantially covers an opening of a needle assembly storage compartment of a needle assembly storage device;
   a pin formed on the barrier and disposed on a lateral surface of the second portion of the arm; and
   a slot receiving the pin, the slot having at least one abutment face for abutting the pin and preventing movement of the barrier in the first direction.

2. The needle assembly reuse prevention mechanism according to claim 1, wherein the barrier comprises:
   a ledge formed on a second lateral surface of the second portion, wherein the ledge at least partially covers the opening of the needle assembly storage compartment and is configured such that a distal end of an injection device applies a force on the ledge when the distal end of the injection device is inserted into the needle storage compartment.

3. The needle assembly reuse prevention mechanism according to claim 1, wherein the barrier comprises:
   a resetting member for engaging the needle assembly storage compartment, wherein the barrier moves in a second direction opposite the first direction when the needle assembly storage compartment is moved and abuts the resetting member.

4. The needle assembly reuse prevention mechanism according to claim 3, wherein the barrier can only move in the second direction when the barrier is in the extended position.

5. The needle assembly reuse prevention mechanism according to claim 1, wherein the at least one abutment face comprises:
   a first abutment face, wherein when the pin abuts the first abutment face, the barrier is in the retracted position;
   a second abutment face, wherein when the pin abuts the second abutment face, the barrier is in an intermediate position; and
   a third abutment face, wherein when the pin abuts the third abutment face, the barrier is in the extended position.

6. The needle assembly reuse prevention mechanism according to claim 5, wherein the pin disengages the first abutment face and the barrier is biased in the first direction into the intermediate position when a force is applied to the second portion in a direction substantially perpendicular to the first direction.

7. The needle assembly reuse prevention mechanism according to claim 6, wherein the pin disengages the second abutment face and the barrier is biased in the first direction into the extended position when the force is applied to the second portion in the direction substantially perpendicular to the first direction.

8. The needle assembly reuse prevention mechanism according to claim 1, wherein the barrier comprises a visual indicator visible to a user only when the barrier is in the extended position.

9. The needle assembly reuse prevention mechanism according to claim 1, wherein the barrier is configured to move in the first direction from the retracted position toward the extended position when an injection device is inserted into the needle assembly storage compartment to couple the injection device to a needle assembly releasably retained in the needle assembly storage compartment.

10. The needle assembly reuse prevention mechanism according to claim 1, wherein the needle storage compartment is one of a plurality of needle storage compartments of the needle assembly storage device, the plurality of needle storage compartments forming an array movably disposed within the needle assembly storage device.

11. The needle assembly reuse prevention mechanism according to claim 10, wherein, when the array is advanced, a projection formed on the needle assembly storage compartment abuts a resetting member on the barrier that moves the barrier in a second direction opposite the first direction toward the retracted position.

12. A needle assembly reuse prevention mechanism comprising:
    a barrier biased in a first direction and movable between a retracted position and an extended position, wherein when in the extended position, the barrier substantially covers an opening of a needle assembly storage compartment of a plurality of needle storage compartments of a needle assembly storage device, the plurality of needle storage compartments forming an array movably disposed within the needle assembly storage device; and
    a pin formed on the barrier; and
    a slot receiving the pin, the slot having at least one abutment face for abutting the pin and preventing movement of the barrier in the first direction,
    wherein the barrier is configured to move in the first direction from the retracted position toward the extended position when an injection device is inserted into the needle assembly storage device to couple the injection device to a needle assembly releasably retained in the needle storage compartment.

13. The needle assembly reuse prevention mechanism according to claim 12, wherein the barrier comprises a stem and an arm, the arm having a first portion connected to the stem and a second portion connected to the first portion at a right angle.

14. The needle assembly reuse prevention mechanism according to claim 13, wherein the stem comprises a spring coupled to the barrier, and the barrier is biased in the first direction by the spring.

15. The needle assembly reuse prevention mechanism according to claim 12, wherein, when the array is advanced, a projection formed on the needle assembly storage compartment abuts a resetting member on the barrier that moves the barrier in a second direction opposite the first direction toward the retracted position.

16. A needle assembly storage device comprising:
    a plurality of needle storage compartments forming an array movably disposed within the needle assembly storage device, a needle assembly storage compartment of the plurality of needle storage compartments comprising an opening;
    a barrier biased in a first direction and movable between a retracted position and an extended position, wherein when in the extended position, the barrier substantially covers the opening; and
    a pin formed on the barrier; and
    a slot receiving the pin, the slot having at least one abutment face for abutting the pin and preventing movement of the barrier in the first direction, wherein the barrier is configured to move in the first direction from the retracted position toward the extended position when an injection device is inserted into the needle assembly storage device to couple the injection device to a needle assembly releasably retained in the needle storage compartment.

17. The needle assembly storage device according to claim 16, wherein the barrier comprises a stem and an arm, the arm having a first portion connected to the stem and a second portion connected to the first portion at a right angle.

18. The needle assembly storage device according to claim 17, wherein the stem comprises a spring coupled to the barrier, and the barrier is biased in the first direction by the spring.

19. The needle assembly storage device according to claim 16, wherein, when the array is advanced, a projection formed on the needle assembly storage compartment abuts a resetting member on the barrier that moves the barrier in a second direction opposite the first direction toward the retracted position.

\* \* \* \* \*